US012674201B2

(12) United States Patent
Wang et al.

(10) Patent No.: US 12,674,201 B2
(45) Date of Patent: Jul. 7, 2026

(54) CHIP, PREPARATION METHOD THEREFOR, AND APPLICATION THEREOF

(71) Applicant: GeneMind Biosciences Co., Ltd., Shenzhen (CN)

(72) Inventors: Qi Wang, Shenzhen (CN); Lei Sun, Shenzhen (CN); Diewen Feng, Shenzhen (CN); Jinhong Gao, Shenzhen (CN); Zhifeng Lin, Shenzhen (GD); Lei Liu, Shenzhen (CN); Fang Chen, Shenzhen (CN)

(73) Assignee: GeneMind Biosciences Co., Ltd., Shenzhen (CN)

( * ) Notice: Subject to any disclaimer, the term of this patent is extended or adjusted under 35 U.S.C. 154(b) by 657 days.

(21) Appl. No.: 18/037,056

(22) PCT Filed: Nov. 11, 2021

(86) PCT No.: PCT/CN2021/129931

§ 371 (c)(1),
(2) Date: May 15, 2023

(87) PCT Pub. No.: WO2022/100637

PCT Pub. Date: May 19, 2022

(65) Prior Publication Data

US 2024/0035084 A1 Feb. 1, 2024

(30) Foreign Application Priority Data

Nov. 16, 2020 (CN) ......................... 202011277986.9

(51) Int. Cl.
*C12Q 1/68* (2018.01)
*C09D 143/04* (2006.01)
*C12Q 1/6874* (2018.01)

(52) U.S. Cl.
CPC ......... *C12Q 1/6874* (2013.01); *C09D 143/04* (2013.01)

(58) Field of Classification Search
None
See application file for complete search history.

(56) References Cited

U.S. PATENT DOCUMENTS 4,908,404 A 3/1990 Benedict et al.
6,602,692 B1 * 8/2003 Glusenkamp .......... C12N 11/06 435/174

(Continued)

FOREIGN PATENT DOCUMENTS

CN 1325456 A 12/2001
CN 101643321 A 2/2010

(Continued)

OTHER PUBLICATIONS

Dugas et al., "Surface Sensitization Techniques and Recognition Receptors Immobilization on Biosensors and Microarraysu", Recognition Receptors in Biosensors, Chapter 2, 2010, pp. 47-134.

(Continued)

*Primary Examiner* — Yung-Sheng M Tsui
*Assistant Examiner* — Melody Tsui
(74) *Attorney, Agent, or Firm* — Kagan Binder, PLLC

(57) ABSTRACT

The present application relates to a chip, a preparation method therefor, and an application thereof. The chip of embodiments of the present application comprises: a substrate having a surface grafted with an amino group, the amino group being a primary amino group or a secondary amino group; and a first compound linked to the surface via the amino group, the first compound comprising the following structure, i.e., formula (1) or formula (2), wherein $R_1$ and $R_2$ are each independently selected from —OH or C1-C5 alkoxy, and n is 1 or 2. The chip can be used for a nucleic (Continued)

acid test, such as single-molecule sequencing and next-generation sequencing.

19 Claims, 2 Drawing Sheets

Specification includes a Sequence Listing.

(56) References Cited

U.S. PATENT DOCUMENTS

| | | | | |
|---|---|---|---|---|
| 6,656,876 | B1 | 12/2003 | Aaberg | |
| 7,241,883 | B2 * | 7/2007 | Lugade | C07C 319/22 435/6.19 |
| 2001/0010902 | A1 | 8/2001 | Kleiber et al. | |
| 2002/0022228 | A1 * | 2/2002 | Nehls | C12Q 1/6834 435/6.12 |
| 2004/0039201 | A1 | 2/2004 | Lugade et al. | |
| 2006/0068204 | A1 | 3/2006 | Rasmussen et al. | |
| 2014/0148500 | A1 * | 5/2014 | Appella | B82Y 5/00 514/44 R |
| 2016/0160272 | A1 | 6/2016 | Mir | |
| 2017/0341075 | A1 | 11/2017 | Sirkis et al. | |
| 2018/0195117 | A1 | 7/2018 | Ge et al. | |
| 2020/0009556 | A1 | 1/2020 | Zimmerley et al. | |
| 2020/0263248 | A1 | 8/2020 | Gremyachinskiy et al. | |
| 2020/0283467 | A1 | 9/2020 | Liu et al. | |
| 2022/0373780 | A1 | 11/2022 | Zheng et al. | |
| 2023/0027811 | A1 | 1/2023 | Li et al. | |

FOREIGN PATENT DOCUMENTS

| | | | | |
|---|---|---|---|---|
| CN | 106345544 | A | 1/2017 | |
| CN | 107305214 | A | 10/2017 | |
| CN | 107486270 | A | 12/2017 | |
| CN | 109490523 | A | 3/2019 | |
| CN | 110511973 | A | 11/2019 | |
| WO | 2009126259 | A1 | 10/2009 | |
| WO | WO-2017202917 | A1 * | 11/2017 | C07H 19/10 |
| WO | 2019091207 | A1 | 5/2019 | |

OTHER PUBLICATIONS

Im et al., "A conformal nano-adhesive via initiated chemical vapor deposition for microfluidic devices", Lab Chip, 2009, vol. 9(3), pp. 411-416.

Kamisetty et al. (2006) "Development of an efficient amine-functionalized glass platform by additional silanization treatment with alkylsilane", Anal. Bioanal. Chem., 386:1649-1655.

Extended European search report for European Application No. 21891157.6, mailed Sep. 24, 2024, 8 pages ..

Gao, Y., et al. (2016) "Single molecule targeted sequencing for cancer gene mutation detection", Scientific Reports, 6(1):1-11.

* cited by examiner

CHIP, PREPARATION METHOD THEREFOR, AND APPLICATION THEREOF

PRIORITY CLAIM

This application claims priority to International Application No. PCT/CN2021/129931. filed Nov. 11, 2021, which claims priority to Chinese Application No. 202011277986.9, filed Nov. 16, 2020, wherein the contents of said applications are incorporated herein by reference in their entireties.

REFERENCE TO SEQUENCE LISTING

This application contains a Sequence Listing in a computer readable form, submitted via EFS-Web. The entire contents of the ASCII text file entitled "GMB0007US Sequence Listing.txt" created on May 15, 2023, and having a size of 996 bytes, is incorporated herein by reference.

TECHNICAL FIELD

The present application relates to the technical field of nucleic acid detection, and in particular, to a chip, a preparation method therefor and application thereof.

BACKGROUND

In recent years, with the rapid development in such fields as big health and precision medicine, the upgrading and progress of nucleic acid detection technologies are receiving more and more attention. Nucleic acid detection chips and related technologies, including capturing of target nucleic acids, specific molecular biological reactions, nucleic acid sequence determination, etc., performed on the surface of a chip, are key factors that determine the performance and application range of nucleic acid detection technologies. In the process of realizing development and upgrading of nucleic acid sequence determination (sequencing) technologies based on chip detection, the first-generation Sanger sequencing, the second-generation sequencing, and the third-generation or fourth-generation single-molecule sequencing are developed.

Various sequencing technologies or sequencing platforms that realize sequencing based on chip detection have their own requirements on the properties of the surface of the chip, the amount of linkage/immobilization or distribution of compounds or sequences thereon, etc. Therefore, for each sequencing technology or sequencing platform, it is generally necessary to develop and design a specific chip that meets specified requirements or can be adapted to the corresponding sequencing platform or sequencing technology.

SUMMARY

Embodiments of the present application provide a chip, which includes: a substrate having a surface grafted with an amino group, the amino group being a primary amino group or a secondary amino group; and a first compound grafted to the surface via the amino group, the first compound including a structure shown below:

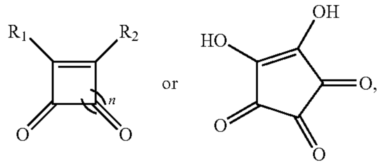

where $R_1$ and $R_2$ are each independently selected from —OH and C1-C5 alkoxy, and n is 1 or 2.

Embodiments of the present application also provide a method for preparing a chip, which can be used to prepare the chip in any one of the embodiments described above. The method includes: obtaining a substrate having a surface grafted with an amino group, the amino group being a primary amino group or a secondary amino group; and linking a first compound to the surface via the amino group, the first compound including the following structure:

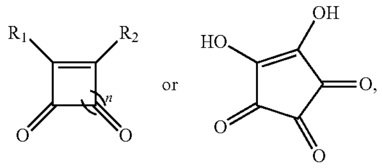

where $R_1$ and $R_2$ are each independently selected from —OH and C1-C5 alkoxy, and n is 1 or 2.

Embodiments of the present application also provide application of the chip according to any one of the embodiments described above or the chip prepared by the method according to any one of the embodiments described above in nucleic acid detection. The nucleic acid detection includes, for example, detection of mutation at a specified site, sequencing, and the like.

The chip according to any one of the embodiments described above or the chip prepared by the method according to any one of the embodiments described above has a uniformly modified surface with high biochemical activity, which is beneficial for controlling the amount and/or density of the subsequently loaded oligonucleotide sequence (primer or probe) and/or nucleic acid molecule under test that are directly or indirectly linked to the first compound. The chip is particularly suitable for the application that poses high requirements on surface properties and needs stable and controllable surface performance.

The chip with the surface properties described above is suitable for a sequencing platform that realizes sequencing based on chip detection and by using the sequencing by synthesis (SBS) principle, such as a single-molecule sequencing platform or a high-throughput sequencing platform, specifically, for example, a platform that allows a nucleic acid molecule under test to be linked to the surface of the chip for single-molecule detection directly without amplification, or for example, a platform that allows a nucleic acid molecule under test to be linked to the surface of the chip and then detected after being amplified into clusters (amplifying signals) on the surface. The chip is suitable for a mainstream platform for realizing sequencing based on the SBS principle currently on the market, such as sequencing platforms of ILLUMINA, BGI and the like. In addition, by using the method according to the above embodiments, the chips with stable and consistent surface properties can be easily and controllably prepared in batches, and have strong industrial practicability.

BRIEF DESCRIPTION OF THE DRAWINGS

The aforementioned and/or additional aspects and advantages of the embodiments of the present application will become apparent and easily understood from the description of the embodiments in reference to the following drawings, among which.

DETAILED DESCRIPTION

Figure 1:
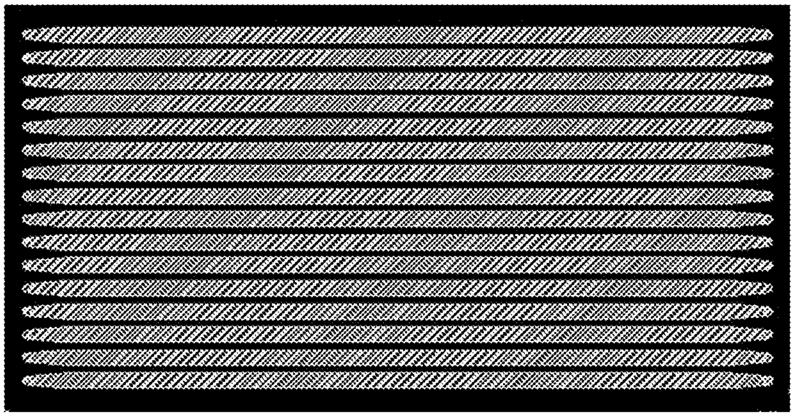
FIG. 1 is a schematic top view of a chip according to an embodiment of the present application.

The chip of the present application, the preparation method therefor and the application thereof are described in further details below with reference to specific examples. The embodiments described below with reference to the accompanying drawings are illustrative and are merely intended to explain the present application, but should not be construed as limiting the present application.

Unless defined otherwise, all technical and scientific terms used herein have the same meaning as commonly understood by those skilled in the art to which the present application belongs. Unless otherwise specified, reagents, detection instruments, etc., in the examples can be self-prepared or are commercially available.

In the present application, the terms "first" and "second" are used for description purpose only rather than being construed as indicating or implying relative importance or implicitly indicating the number of indicated technical features. Therefore, features defined with "first" and "second" may explicitly or implicitly include at least one of the features. In the present application, unless otherwise specifically defined, "a plurality of" means two or more.

"Linking" as used herein should be comprehended in its broad sense. For example, it may be direct connection or indirect connection through an intermediate, and it may be chemical ligation or physical connection. Unless otherwise specifically defined, in the present application, with regard to the description of the linking relation involving compounds, biomolecules, groups, etc., the linking generally refers to chemical ligation, such as binding by a covalent bond, adsorption based on Van der Waals' force or electrostatic interaction, or the like. For those skilled in the art, the specific meanings of the above terms herein can be understood according to specific conditions.

The "grafted to . . . via . . . " or "modified with" as used herein may refer to a direct graft to or modification with an object, or may refer to an indirect graft to or modification with the object, for example, via other groups or structures. Unless otherwise specifically stated, link as used herein includes grafting, immobilization, binding, and the like, and, unless otherwise specifically stated, grafting, immobilization, binding and covalent linking/covalent binding (linking via a covalent bond) are used interchangeably herein. The amino group as used herein is a group containing the structure —$N(X)_2$, where each "X" is independently H, substituted or unsubstituted alkyl, substituted or unsubstituted cycloalkyl, substituted or unsubstituted heterocyclyl, or the like; in embodiments of the present application, unless otherwise specifically stated, at least one X is H. The amino group includes, but is not limited to, —$NH_2$, —NH(alkyl), —NH(cycloalkyl), —NH(heterocyclyl) and —NH(aryl).

The "alkyl" refers to a saturated hydrocarbon containing a primary (normal) carbon atom, a secondary carbon atom, a tertiary carbon atom, a quaternary carbon atom, or a combination thereof. Alkyl includes, but is not limited to: methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl(—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$ and octyl (—$(CH_2)_7CH_3$).

The "alkoxy" refers to alkyl containing an —O— group, such as a group formed by linking the alkyl listed above to an oxygen atom. The "C1-C5 alkoxy" means that the alkyl moiety contains 1-5 carbon atoms, and it may be independently C1 alkoxy, C2 alkoxy, C3 alkoxy, C4 alkoxy or C5 alkoxy at each occurrence. Suitable examples include, but are not limited to: methoxy (—O—$CH_3$ or —OMe), ethoxy (—O—$CH_2CH_3$ or -OEt) and tert-butoxy (—O—$C(CH_3)_3$ or -OtBu).

The various types of silanes as used herein refer to silicon hydrocarbons. For example, the aminosilane, alkenylsilane, alkynylsilane, etc., refer to silicon hydrocarbons containing a corresponding group or bond; for example, aminosilane refers to silicon hydrocarbon containing at least one amino group, alkenylsilane refers to silicon hydrocarbon containing at least one double bond, and alkynylsilane refers to silicon hydrocarbon containing at least one triple bond.

The "structural unit" as used herein refers to a repeating unit typically included in a polymer/high polymer, and is sometimes referred to as a monomer (monomer unit), a repeating unit or a mer. A polymer may include one or more structural units. A high polymer may be polymerized from one monomer or from a plurality of monomers.

The chip as used herein is a solid support or a solid substrate, and it may be a substrate grafted with silane, polymer or a squaric acid compound, or a substrate further grafted with a nucleic acid sequence on a polymer or a squaric acid compound. The material of which the substrate is made is not particularly limited, and it is, for example, at least one selected from glass, silicon wafer, plastic, gel and nylon film. Unless otherwise specifically stated, the surface of a chip and the surface of a substrate are used interchangeably.

The nucleic acid sequence as used herein may be DNA and/or RNA. The "probe" is a nucleic acid sequence of known sequence, and it may be DNA and/or RNA, and the like. In some embodiments, it is also referred to as a "primer". It is typically an oligonucleotide strand of less than 150 nt in length. By structurally and/or chemically treating the surface of the substrate, the probes linked to the surface can be made to be randomly or regularly distributed.

The chip provided in the embodiments of the present application includes a first chip, which includes: a substrate having a surface grafted with an amino group, the amino group being a primary amino group or a secondary amino group; and a first compound grafted to the surface via the amino group, the first compound including a structure shown below:

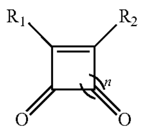

or

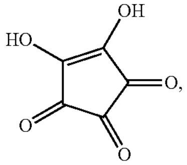

where $R_1$ and $R_2$ are each independently selected from —OH and C1-C5 alkoxy, and n is 1 or 2.

The chip has a uniformly modified surface with high biochemical activity by containing a modification layer having the first compound with the structural characteristic described above, which is beneficial for controlling the amount and/or density of the subsequently loaded oligonucleotide sequence (primer or probe) and/or nucleic acid molecule under test that are directly or indirectly linked to the first compound. The chip with the surface properties is suitable for a single-molecule sequencing platform or a second-generation sequencing platform, for example, a platform that allows a nucleic acid molecule under test to be linked to the surface of the chip for single-molecule detection directly without amplification, or for example, a platform that allows a nucleic acid molecule under test to be linked to the surface of the chip and then detected after being amplified into clusters (amplifying signals) on the surface. The chip is suitable for mainstream second-generation sequencing platforms on the market, such as sequencing platforms of ILLUMINA based on sequencing by synthesis. In addition, the chip is easy to prepare, including easy to steadily prepare a surface having consistent reproducible properties, and has strong industrial practicability.

The alkoxy herein is a linear and/or branched oxygen-containing alkyl, and it may be, for example, $—OCH_3$, $—OCH_2CH_3$, $—O(CH_2)_mCH_3$ (m=2-4), $—OCH(CH_3)_2$, $—OC(CH_3)_3$, $—OCH(CH_3)CH_2CH_3$, $—OCH(CH_3)CH_2CH_2CH_3$, $—OCH(CH_3)CH_2CH_3$, $—OC(CH_3)_2CH_2(CH_3)_2$, $—OCH_2CH(CH_3)_2$, or the like.

In certain examples, $R_1$ and $R_2$ are each independently selected from —OH, $—OCH_3$ and $—OCH_2CH_3$.

In certain examples, the first compound includes one of the following structures:

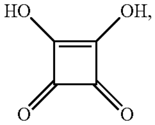

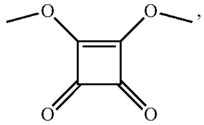

-continued

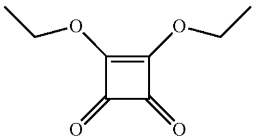

, or

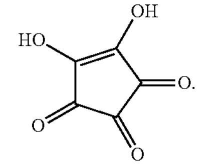

The first compound including any of the structures described above may impart the surface with the property of high reactivity and may enable the surface to react with a variety of compounds/groups containing an amino group. After the squaric acid in the four first compounds described above is grafted to the amino group of aminosilane, the squaric acid may also continue to react with other compounds containing an amino group, such as nucleic acids, polylysine, etc., that contain an amino group, thereby enabling more flexible selection of compounds capable of participating in the reaction on the surface of the substrate and possibly allowing the resulting surface to have richer or more manageable properties. By utilizing the properties of the first compound, different compounds containing an amino group can be selected to react with the first compound according to the requirements of various applications on the amount/density of probes on the surface. For example, if the polymer macromolecule polylysine is selected to react with squaric acid and the polymer macromolecule is immobilized on the surface of a chip substrate, the density of active groups related to the immobilization of the probes on the surface of the chip can be improved.

In certain examples, the amino group is derived from at least one of aminosilane, polylysine, polyornithine, chitosan, polyamidoamine dendrimer, polyacrylamide and polyethyleneimine compounds. As such, it is beneficial for forming a surface having the properties described above.

Specifically, in certain examples, the amino group is derived from a polymer, such as polylysine, polyornithine, chitosan, polyamidoamine dendrimer or polyacrylamide. As such, a greater amount/higher density of amino groups may be provided for linking to the first compound, which facilitates the control or improvement of the amount/density of the first compound on the surface and thereby facilitates the control or improvement of the amount/density of molecules further linked to the first compound. In certain examples, the amino group is derived from the aminosilane. Specifically, the aminosilane may be selected from at least one of (3-aminopropyl)triethoxysilane, 3-aminopropyl trimethoxysilane, 3-aminopropyl methyldiethoxysilane and aminoethylaminopropyl triethoxysilane.

In certain examples, the substrate having the surface grafted with the amino group includes silane linked to the surface and a polymer linked to the surface via the silane, where the silane is selected from at least one of epoxy silane, alkenylsilane, and alkynylsilane, and the polymer includes a plurality of structural units, at least one of which includes the amino group.

In certain examples, the polymer is selected from at least one of polylysine, polyornithine, chitosan, polyamidoamine dendrimer, polyacrylamide and polyethyleneimine compounds.

In certain examples, the silane includes the epoxy silane selected from at least one of 3-glycidoxypropyltrimethoxysilane, 3-glycidoxypropyltriethoxysilane, 3-glycidoxypropylmethyldiethoxysilane and 3-glycidoxypropylmethyldimethoxysilane.

In certain examples, the silane includes the alkenylsilane selected from at least one of vinyltrimethoxysilane, vinyltriethoxysilane, vinyltris(2-methoxyethoxy)silane and vinyltriisopropoxysilane.

In certain examples, the silane includes the alkynylsilane selected from at least one of propynyloxytrimethoxysilane and 2-propynyl [3-(triethoxysilyl)propyl]carbamate.

In certain examples, the chip further includes a nucleic acid sequence having an amino modification on at least one terminus and linked to the first compound.

In certain examples, the chip further includes a polymer linked to the first compound, where the polymer includes a plurality of structural units, at least one of the structural units including an amino group.

In certain examples, the chip further includes a nucleic acid sequence linked to the polymer.

In certain examples, the polymer and the nucleic acid sequence are linked via a linker group including a first terminus capable of bonding to the nucleic acid sequence and a second terminus capable of linking to the amino group of the polymer.

In certain examples, the second terminus includes at least one of —NHS, an epoxy group and an isocyanate group.

In certain examples, the nucleic acid sequence has a -DBCO or —$N_3$ modification, and the first terminus includes -DBCO or —$N_3$.

In certain examples, the polymer is selected from at least one of polylysine, polyornithine, chitosan, polyamidoamine dendrimer, polyacrylamide and polyethyleneimine compounds.

The chip provided in the embodiments of the present application includes a second chip, which includes: a substrate having a surface grafted with an amino group, the amino group being a primary amino group or a secondary amino group; and a first compound grafted to the surface of the substrate via the amino group, the first compound having the structural characteristic shown below:

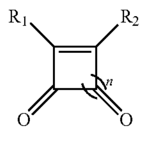

or

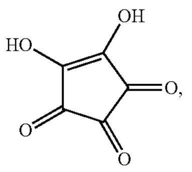

where $R_1$ and $R_2$ are each independently selected from —OH and C1-C5 alkoxy; n is 1 or 2; the substrate having the surface grafted with the amino group includes a backing layer, silane grafted on the backing layer and a polymer grafted to the silane, where the silane is selected from at least one of epoxy silane, alkenylsilane and alkynylsilane, and at least one structural unit of the polymer includes the amino group.

Specifically, in certain examples, the alkyl in the alkoxy may be linear alkyl or alkyl containing a branched chain, and may be, for example, —$OCH_3$, —$OCH_2CH_3$, —$O(CH_2)_mCH_3$ (m=2-4), —$OCH(CH_3)_2$, —$OC(CH_3)_3$, —$OCH(CH_3)CH_2CH_3$, —$OCH(CH_3)CH_2CH_2CH_3$, —$OCH(CH_3)CH_2CH_3$, —$OC(CH_3)_2CH_2(CH_3)_2$, —$OCH_2CH(CH_3)_2$, or the like. In a certain specific embodiment, $R_1$ and $R_2$ are each independently selected from —OH, —$OCH_3$ and —$OCH_2CH_3$.

In a certain specific embodiment, the first compound is selected from one of the following compounds:

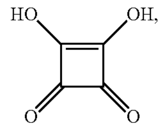

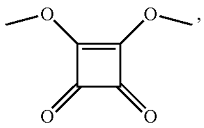

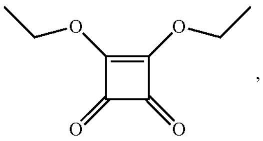

, or

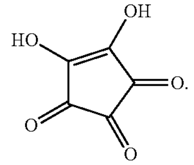

In a certain specific embodiment, the polymer is selected from at least one of polylysine, polyornithine, chitosan, polyamidoamine dendrimer, polyacrylamide and polyethyleneimine compounds.

In a certain specific embodiment, the silane includes the epoxy silane that may be selected from at least one of 3-glycidoxypropyltrimethoxysilane, 3-glycidoxypropyltriethoxysilane, 3-glycidoxypropylmethyldiethoxysilane and 3-glycidoxypropylmethyldimethoxysilane.

In certain examples, the silane includes the alkenylsilane that may be selected from at least one of vinyltrimethoxysilane, vinyltriethoxysilane, vinyltris(2-methoxyethoxy)silane and vinyltriisopropoxysilane.

In certain examples, the silane includes the alkynylsilane that may be selected from at least one of propynyloxytrimethoxysilane and 2-propynyl [3-(triethoxysilyl)propyl] carbamate.

It can be understood that the second chip of this embodiment may also have additional technical features and technical effects of the chip or the first chip in any one of the embodiments described above, which will not be repeated here.

The chip provided in the embodiments of the present application includes a third chip, which includes: a substrate having a surface grafted with an amino group, the amino group being a primary amino group or a secondary amino group; a first compound grafted to the surface via the amino group; and a second compound grafted to the first compound, the second compound including an amino group; the first compound has the structural characteristic shown below:

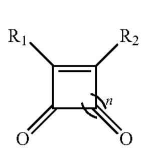

or

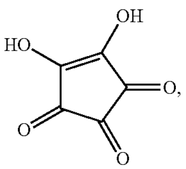

where $R_1$ and $R_2$ are each independently selected from —OH and C1-C5 alkoxy, and n is 1 or 2.

Specifically, in certain examples, the alkyl in the alkoxy may be straightly-linked alkyl or alkyl containing a branched chain, and may be, for example, —$OCH_3$, —$OCH_2CH_3$, —$O(CH_2)_mCH_3$ (m=2-4), —$OCH(CH_3)_2$, —$OC(CH_3)_3$, —$OCH(CH_3)CH_2CH_3$, —$OCH(CH_3)CH_2CH_2CH_3$, —$OCH(CH_3)CH_2CH_3$, —$OC(CH_3)_2CH_2(CH_3)_2$, —$OCH_2CH(CH_3)_2$, or the like. In a certain specific embodiment, $R_1$ and $R_2$ are each independently selected from —OH, —$OCH_3$ and —$OCH_2CH_3$.

In certain examples, the first compound is selected from one of the following compounds:

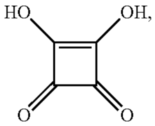 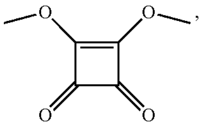,

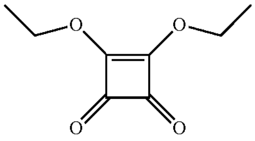, or 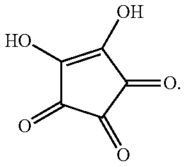

In certain examples, the second compound is a nucleic acid sequence with an amino modification.

Specifically, in a certain example, the nucleic acid sequence is a nucleic acid sequence of known sequence, and it can be used as a probe or a primer for capturing a target sequence and/or performing amplification or sequencing assays, and the like. As for reacting the first compound with the modifying amino group of the nucleic acid sequence to link the nucleic acid sequence to the surface of the chip, it can be understood that the amount of the active group involved in the reaction contained in the first compound directly affects the amount of the nucleic acid sequence linked to the surface.

In certain examples, the second compound is a polymer whose at least one structural unit includes an amino group.

Further, in certain examples, the chip further includes a nucleic acid sequence linked to the second compound via a linker group.

In certain examples, the linker group has a molecular structure containing a first linker group and a second linker group. The first linker group is bonded to the nucleic acid sequence, and the second linker group is grafted to the polymer via the amino group contained in the polymer.

In certain examples, the second linker group is selected from at least one of an —NHS group, an epoxy group and an isocyanate group. Preferably, the second linker group is —NHS. The reaction of —NHS with an amino group is easy to operate and control and can be carried out at room temperature with a pH of 7-9.

In certain examples, at least one terminus of the nucleic acid sequence is modified with -DBCO or —$N_3$, the first linker group is selected from a -DBCO group and a —$N_3$ group, and the first linker group is covalently bonded to the nucleic acid sequence through the -DBCO group and the —$N_3$ group. It can be understood that when the modifying group of the nucleic acid sequence is -DBCO, the first linker group is —$N_3$; when the modifying group of the nucleic acid sequence is —$N_3$, the first linker group is -DBCO.

In certain examples, the polymer is selected from at least one of polylysine, polyornithine, chitosan, polyamidoamine dendrimer, polyacrylamide and polyethyleneimine compounds.

Specifically, in certain examples, the second compound is a polymer whose at least one structural unit contains the amino group, such as polylysine, polyornithine, chitosan, polyamidoamine dendrimer or polyacrylamide. Since the structure of the polymer itself includes a steric structure formed on the surface, the polymer can provide a greater amount/higher density of amino groups on the surface of the substrate, thereby increasing the density of the immobilized nucleic acid sequence.

It can be understood that the third chip according to any one of the embodiments described above may also have additional technical features and technical effects of the chip, the first chip or the second chip according to any one of the embodiments described above, which will not be repeated here.

A method for preparing a chip provided in the embodiments of the present application can be used to prepare the chip in any one of the embodiments described above. The method includes: obtaining a substrate having a surface grafted with an amino group, the amino group being a primary amino group or a secondary amino group; and linking a first compound to the surface via the amino group, the first compound including the following structure:

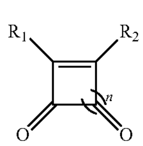 or 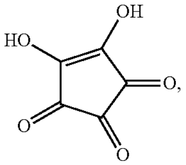

where $R_1$ and $R_2$ are each independently selected from —OH and C1-C5 alkoxy, and n is 1 or 2.

In certain examples, $R_1$ and $R_2$ are each independently selected from —OH, —$OCH_3$ and —$OCH_2CH_3$.

In certain examples, the first compound is selected from one of the following compounds:

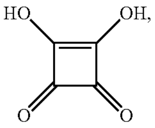 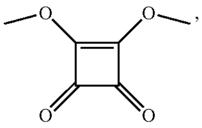,

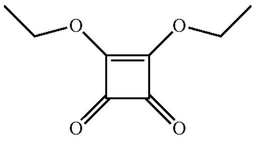 or 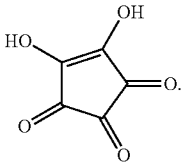

In certain examples, the amino group is derived from at least one of aminosilane, polylysine, polyornithine, chitosan, polyamidoamine dendrimer, polyacrylamide and polyethyleneimine compounds.

In certain examples, a reaction is performed at room temperature for 3-5 h to allow the amino group to be linked to the first compound.

In certain examples, the amino group is derived from the aminosilane. Specifically, the aminosilane is selected from at least one of (3-aminopropyl)triethoxysilane, 3-aminopropyl trimethoxysilane, 3-aminopropyl methyldiethoxysilane and aminoethylaminopropyl triethoxysilane.

In certain examples, a reaction is performed at room temperature for 1-8 h to allow the aminosilane to be linked to the surface, in order to obtain the substrate having the surface grafted with the amino group.

In certain examples, the substrate having the surface grafted with the amino group includes silane linked to the surface and a polymer linked to the surface via the silane, where the silane is selected from at least one of epoxy silane, alkenylsilane, and alkynylsilane, and the polymer includes a plurality of structural units, at least one of which includes the amino group.

Specifically, in certain examples, the polymer is selected from at least one of polylysine, polyornithine, chitosan, polyamidoamine dendrimer, polyacrylamide and polyethyleneimine compounds.

In certain examples, the silane includes the epoxy silane selected from at least one of 3-glycidoxypropyltrimethoxysilane, 3-glycidoxypropyltriethoxysilane, 3-glycidoxypropylmethyldiethoxysilane and 3-glycidoxypropylmethyldimethoxysilane.

In certain examples, the silane includes the alkenylsilane selected from at least one of vinyltrimethoxysilane, vinyltriethoxysilane, vinyltris(2-methoxyethoxy)silane and vinyltriisopropoxysilane.

In certain examples, the silane includes the alkynylsilane selected from at least one of propynyloxytrimethoxysilane and 2-propynyl [3-(triethoxysilyl)propyl]carbamate.

In certain examples, a reaction is performed at room temperature for 1-8 h to allow the silane to be linked to the surface.

In certain examples, a reaction is performed at 30-65° C. for 1-48 h to allow the polymer to be linked to the silane.

In certain examples, the method further includes: linking a nucleic acid sequence having an amino modification on at least one terminus to the first compound via the amino modification.

Specifically, in certain examples, the method further includes: treating the surface with a blocking reagent selected from at least one of NHS-PEG4, NHS-PEG4-NHS, NHS-PEG-N 3 and acetic anhydride.

In certain examples, a reaction is performed at 30-80° C. for 1-48 h to allow the nucleic acid sequence to be linked to the first compound.

In certain examples, the method further includes: linking a polymer to the first compound, where the polymer includes a plurality of structural units, at least one of which includes an amino group.

Further, the method also includes: linking a nucleic acid sequence to the polymer via a linker group, wherein the linker group includes a first terminus capable of linking to the nucleic acid sequence and a second terminus capable of linking to the amino group of the polymer.

Specifically, in certain examples, the method further includes: treating the surface with a blocking reagent selected from at least one of NHS-PEG4, NHS-PEG4-NHS, NHS-PEG-N3 and acetic anhydride.

In certain examples, the nucleic acid sequence has a -DBCO or —$N_3$ modification, and the first terminus includes -DBCO or —$N_3$.

In certain examples, the second terminus includes at least one of an —NHS group, an epoxy group and an isocyanate group.

In certain examples, the first terminus of the linker group is linked to the nucleic acid sequence by reacting at 30-65° C. for 1-48 h.

In certain examples, a reaction is performed at room temperature for 0.5-5 h to allow the second terminus of the linker group to be linked to the amino group of the polymer.

In certain examples, the polymer is selected from at least one of polylysine, polyornithine, chitosan, polyamidoamine dendrimer, polyacrylamide and polyethyleneimine compounds.

In certain examples, a reaction is performed at 30-40° C. for 1-5 h to allow the polymer to be linked to the first compound.

The preparation method provided in the embodiments of the present application includes a first preparation method, which includes the following steps: (1) obtaining a substrate having a surface grafted with an amino group, the amino group being a primary amino group or a secondary amino group; (2) grafting a first compound to the amino group, the first compound having the structural characteristic shown below:

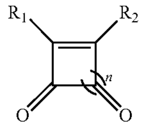

or

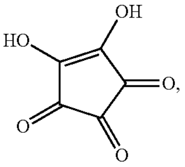

where $R_1$ and $R_2$ are each independently selected from —OH and C1-C5 alkoxy, and n is 1 or 2.

This method is simple and convenient to operate, and is able to prepare a chip having a surface containing the first compound modification layer with the specific structural characteristic described above. Besides, the modification layer on the surface of the prepared chip is high in biochemical reaction activity and good in repeatability and stability. The prepared chip is suitable for nucleic acid detection based on chip detection, and can regulate and control the amount and density of the subsequently loaded oligonucleotide sequence (primer or probe) and/or nucleic acid molecule under test that are directly or indirectly linked to the first compound. The chip with the surface properties described above prepared by this method is suitable for a single-molecule sequencing platform or a second-generation sequencing platform, for example, a platform that allows a nucleic acid molecule under test to be linked to the surface of the chip for detection directly without amplification, or for example, a platform that allows a nucleic acid molecule under test to be linked to the surface of the chip and then detected after being amplified into clusters (amplifying signals) on the surface. The chip is suitable for mainstream second-generation sequencing platforms on the market, such as sequencing platforms of ILLUMINA and BGI.

The alkyl in the alkoxy described above may be straightly-linked alkyl or alkyl containing a branched chain, and may be, for example, —$OCH_3$, —$OCH_2CH_3$, —$O(CH_2)_mCH_3$ (m=2-4), —$OCH(CH_3)_2$, —$OC(CH_3)_3$, —$OCH(CH_3)CH_2CH_3$, —$OCH(CH_3)CH_2CH_2CH_3$, —$OCH(CH_3)CH_2CH_3$, —$OC(CH_3)_2CH_2(CH_3)_2$, —$OCH_2CH(CH_3)_2$, or the like. In a certain specific embodiment, $R_1$ and $R_2$ are each independently selected from —OH, —$OCH_3$ and —$OCH_2CH_3$.

In a certain specific embodiment, the first compound is selected from one of the following compounds:

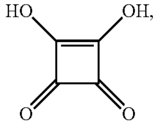

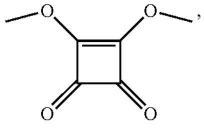

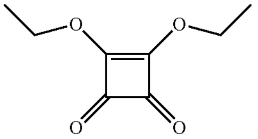

or

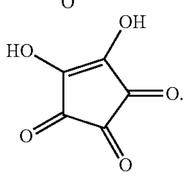

The first compound has the property of high reactivity and can be used as a linker for a variety of compounds containing an amino group. After the squaric acid in the four first compounds described above is grafted to the aminosilane, the squaric acid may also continue to react with other compounds containing an amino group, such as amino group-containing nucleic acids, polylysine, etc. Thus, preparing chips using the first compound increases the flexibility of selecting additional compounds needed for preparing the surface of a chip substrate. When preparing chips with such compounds, different compounds containing an amino group can be selected to react with the first compound according to the different requirements on the density of probes on the chip. For example, if the polymer macromolecule polylysine is selected to react with squaric acid and the polymer macromolecule is immobilized on the surface of a chip substrate, the density of active groups related to the immobilization of the probes on the surface of the chip can be improved.

In a certain specific embodiment, the grafting described above is reacting at room temperature for 3-5 h.

In a certain specific embodiment, the amino group described above is derived from at least one of aminosilane, polylysine, polyornithine, chitosan, polyamidoamine dendrimer, polyacrylamide and polyethyleneimine compounds.

In a certain specific embodiment, the amino group described above is derived from the aminosilane, and substrate grafted with the amino group includes a backing layer and the aminosilane grafted on the backing layer.

In a certain specific embodiment, the aminosilane described above is selected from at least one of (3-aminopropyl)triethoxysilane, 3-aminopropyl trimethoxysilane, 3-aminopropyl methyldiethoxysilane and aminoethylaminopropyl triethoxysilane.

In a certain specific embodiment, the aminosilane described above is grafted on the backing layer by reacting at room temperature for 1-8 h.

The preparation method provided in the embodiments of the present application includes a second preparation method, which includes the following steps: (1) obtaining a substrate grafted with an amino group, the amino group being a primary amino group or a secondary amino group; (2) grafting a first compound to the amino group, where the substrate grafted with the amino group includes silane grafted on the surface and a polymer grafted to the silane, the silane is selected from at least one of epoxy silane, alkenylsilane and alkynylsilane, at least one structural unit of the polymer includes the amino group, and the first compound has the structural characteristic shown below:

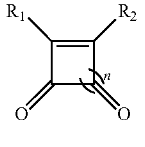

or

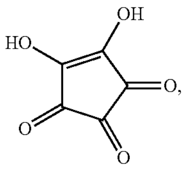

, where $R_1$ and $R_2$ are each independently selected from —OH and C1-C5 alkoxy, and n is 1 or 2.

In a certain specific embodiment, the first compound is selected from one of the following compounds:

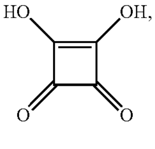

,

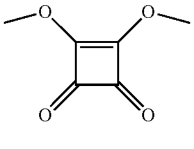

,

-continued

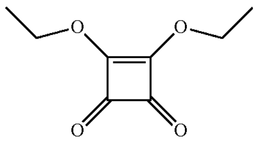

and

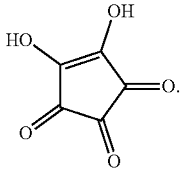

.

In a certain specific embodiment, the polymer is selected from at least one of polylysine, polyornithine, chitosan, polyamidoamine dendrimer, polyacrylamide and polyethyleneimine compounds. The steric structure of the polymer containing an amino group may provide a higher density of amino groups, and thus the density of the first compound grafted with the amino group may be increased.

In a certain specific embodiment, the epoxy silane is selected from at least one of 3-glycidoxypropyltrimethoxysilane, 3-glycidoxypropyltriethoxysilane, 3-glycidoxypropylmethyldiethoxysilane and 3-glycidoxypropylmethyldimethoxysilane; the alkenylsilane is selected from at least one of vinyltrimethoxysilane, vinyltriethoxysilane, vinyltris(2-methoxyethoxy)silane and vinyltriisopropoxysilane; the alkynylsilane is selected from at least one of propynyloxytrimethoxysilane and 2-propynyl [3-(triethoxysilyl)propyl] carbamate.

In a certain specific embodiment, the silane is grafted on the surface by reacting at room temperature for 1-8 h.

In a certain specific embodiment, the polymer is grafted on the silane by reacting at 30-65° C. for 1-48 h.

It can be understood that the second preparation method according to any one of the embodiments described above may also have additional technical features and technical effects of the method according to any one of the embodiments described above, which will not be repeated here.

The preparation method provided in the embodiments of the present application includes a third preparation method, which includes the following steps: (1) obtaining a substrate having a surface grafted with an amino group, the amino group being a primary amino group or a secondary amino group; (2) grafting a first compound to the amino group; and (3) grafting a second compound on the first compound, where the second compound includes an amino group, and the first compound has the structural characteristic shown below:

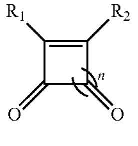

or

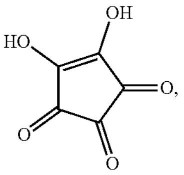

, where $R_1$ and $R_2$ are each independently selected from —OH and C1-C5 alkoxy, and n is 1 or 2.

In certain examples, the alkyl in the alkoxy may be straightly-linked alkyl or alkyl containing a branched chain, and may be, for example, $—OCH_3$, $—OCH_2CH_3$, $—O(CH_2)_mCH_3$ (m=2-4), $—OCH(CH_3)_2$, $—OC(CH_3)_3$, $—OCH(CH_3)CH_2CH_3$, $—OCH(CH_3)CH_2CH_2CH_3$, $—OCH(CH_3)CH_2CH_3$, $—OC(CH_3)_2CH_2(CH_3)_2$, $—OCH_2CH(CH_3)_2$, or the like. In a certain specific embodiment, $R_1$ and $R_2$ are each independently selected from —OH, $—OCH_3$ and $—OCH_2CH_3$.

In a certain specific embodiment, the first compound is selected from one of the following compounds:

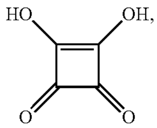
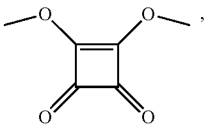

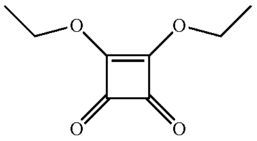
and
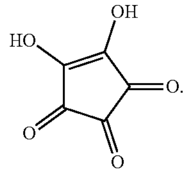

In a certain specific embodiment, the second compound is an amino group-modified nucleic acid sequence.

In a certain specific embodiment, the method further includes step (4): performing blocking treatment on the amino group on the surface of the chip by using a blocking reagent.

By blocking amino groups on the surface of the chip that haven't participated in the reaction or that are incompletely reacted using the blocking reagent, the nonspecific adsorption of the amino groups on the surface of the chip to proteins and/or nucleic acid sequences, such as DNA polymerase and template nucleic acid sequences, can be reduced, thereby reducing the influence on sequencing, nucleic acid hybridization or other experimental procedures. Any reagent that can theoretically remove the amino group activity without affecting the subsequent experimental process can be used as the blocking reagent. For example, the blocking reagent may be selected from, but is not limited to, at least one of NHS-PEG4, NHS-PEG4-NHS, NHS-PEG-$N_3$ and acetic anhydride.

Preferably, in a certain specific embodiment, the blocking reagent is NHS-PEG4.

In a certain specific embodiment, a reaction is performed at 30-80° C. for 1-48 h to allow the nucleic acid sequence to be grafted to the first compound.

It can be understood that the third preparation method may also have additional technical features and advantages of the method according to any one of the embodiments described above, which will not be repeated here.

The preparation method provided in the embodiments of the present application includes a fourth preparation method, which includes the following steps: (1) obtaining a substrate having a surface grafted with an amino group, the amino group being a primary amino group or a secondary amino group; (2) grafting a first compound to the amino group; and (3) grafting a second compound on the first compound, where the second compound is a polymer whose at least one structural unit includes an amino group, and the first compound has the structural characteristic shown below:

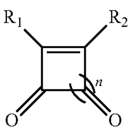
or
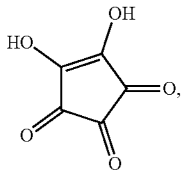

where $R_1$ and $R_2$ are each independently selected from —OH and C1-C5 alkoxy, and n is 1 or 2.

In certain examples of the fourth preparation method, the alkyl in the alkoxy may be straightly-linked alkyl or alkyl containing a branched chain, and may be, for example, $—OCH_3$, $—OCH_2CH_3$, $—O(CH_2)_mCH_3$ (m=2-4), $—OCH(CH_3)_2$, $—OC(CH_3)_3$, $—OCH(CH_3)CH_2CH_3$, $—OCH(CH_3)CH_2CH_2CH_3$, $—OCH(CH_3)CH_2CH_3$, $—OC(CH_3)_2CH_2(CH_3)_2$, $—OCH_2CH(CH_3)_2$, or the like. In a certain specific embodiment. $R_1$ and $R_2$ are each independently selected from —OH, $—OCH_3$ and $—OCH_2CH_3$.

In a certain specific embodiment, the first compound is selected from one of the following compounds:

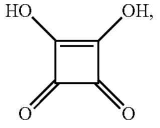
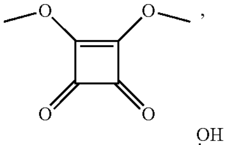

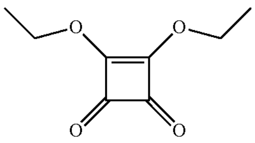
and
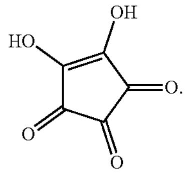

In a certain specific embodiment, the method further includes step (4): grafting a nucleic acid sequence to the second compound through a linker group, where the linker group has a molecular structure containing a first linker group and a second linker group, the first linker group is bonded to the nucleic acid sequence, and the second linker group is grafted to the polymer via the amino group contained in the polymer.

In a certain specific embodiment, the method further includes step (5): performing blocking treatment on the amino group on the surface of the chip by using a blocking reagent.

By blocking amino groups on the surface of the chip that haven't participated in the reaction or that are incompletely reacted using the blocking reagent, the nonspecific adsorption of the amino groups on the surface of the chip to proteins and/or nucleic acid sequences, such as DNA polymerase and template nucleic acid sequences, can be reduced, thereby reducing the influence on sequencing, nucleic acid hybridization or other experimental procedures. Any reagent that can theoretically remove the amino group activity without affecting the subsequent experimental process can be used as the blocking reagent. For example, the blocking reagent may be selected from, but is not limited to, at least one of NHS-PEG4, NHS-PEG4-NHS, NHS-PEG-$N_3$ and acetic anhydride. In a certain specific embodiment, the blocking reagent is preferably acetic anhydride.

In a certain specific embodiment, the nucleic acid sequence described above is modified with a -DBCO group or a $—N_3$ group, the first linker group is selected from a -DBCO group and a $—N_3$ group, and the first linker group is covalently bonded to the nucleic acid sequence through the -DBCO group and the $—N_3$ group. It can be understood that when the modifying group of the nucleic acid sequence is -DBCO, the first linker group is $—N_3$; when the modifying group of the nucleic acid sequence is $—N_3$, the first linker group is -DBCO.

In a certain specific embodiment, a reaction is performed at room temperature for 0.5-5 h to allow the second linker group to be grafted to the second compound. In a certain specific embodiment, a reaction is performed at 30-65° C. for 1-48 h to allow the first linker group to be covalently bonded and the nucleic acid sequence.

In a certain specific embodiment, the polymer is selected from at least one of polylysine, polyornithine, chitosan, polyamidoamine dendrimer, polyacrylamide and polyethyleneimine compounds. When the second compound is a polymer whose at least one structural unit contains the amino group, such as polylysine, polyornithine, chitosan, polyamidoamine dendrimer or polyacrylamide, the polymer can provide a higher density of amino groups on the surface of the chip substrate due to the steric structure of the polymer itself, thereby increasing the density of the immobilized nucleic acid sequence.

In a certain specific embodiment, a reaction is performed at 30-40° C. for 1-5 h to allow the polymer to be grafted to the first compound.

It can be understood that the fourth preparation method in any one of the embodiments described above may also have additional technical features and advantages of the method according to any one of the embodiments described above, which will not be repeated here.

Embodiments of the present application also provide application/use of the chip according to any one of the embodiments described above or the chip prepared by the method according to any one of the embodiments described above in nucleic acid detection. It can be understood that the applications/uses may include applications aimed at the diagnosis and treatment of diseases, and may also include applications not aimed at the diagnosis and treatment of diseases, such as the detection of microorganisms in the air, the detection of microorganisms in contaminated water, the pathological detection of dead animals, etc.

In a certain specific embodiment, the nucleic acid detection described above is sequencing, such as single-molecule sequencing or second-generation sequencing.

In practical application, one or more of the following procedures can be performed on the chip as required: (1) Detecting the probe density: a nucleic acid strand with a fluorophore is hybridized with a probe on the surface of the chip for detecting the density of the probe;

(2) Photographing and calculating the number/density of fluorescence molecules on the surface: under a high-power fluorescence microscope, a plurality of fields of view on the surface of the chip are photographed, the number of spots (bright dots) in the images is counted by using image software such as ImageJ software, and the average number of (bright) dots in a field of view is calculated, thus deducing the density of fluorescent molecules; or under a common fluorescence microscope, a plurality of fields of view on the surface of the chip are photographed, and the relative density of the fluorescent molecules on the surface is calculated through the local or overall brightness of the pictures; the measured amount/density of the probes on the surface guides the treatment conditions in the subsequent application procedures;

(3) Measuring the ratio of single molecules after hybridization (for single-molecule sequencing chips): how many bright dots in all the bright dots after hybridization are fluorescence emitted by one fluorescent molecule is detected by photographing under continuous exposure (movie) with a single-molecule fluorescence microscope;

(4) Amplification on the surface of chip (for second-generation sequencing): the nucleic acid amplification is performed on the surface of the chip by such methods as bridge PCR, recombinase polymerase amplification (RPA), template walking, and the like, or the beads in the emulsion PCR are directly loaded on the surface of the chip.

The following are specific examples. Unless otherwise specified, all experimental materials are from commercial suppliers or are synthesized/prepared by a contractor (e.g., Aladdin, Sigma, Sangon, etc.).

Single-molecule sequencing platforms such as Genocare™1600 referred to herein are commercial automated sequencing platforms based on the sequencing by synthesis (SBS) principle and using virtual terminators and TIRF optical detection systems to determine the order of nucleotides or bases of nucleic acid molecules. Reference can be made to the technical schemes disclosed in the article Single molecule targeted sequencing for cancer gene mutation detection (*Scientific Reports,* 6:26110, DOI: 10.1038/srep26110), disclosed patent applications such as CN201680047468.3, CN201910907555.7, CN201880077576.4 and/or CN201911331502.1, and the like, for the construction of platforms/functional modules and the preparation of suitable reagents/consumables. The Genocare1600 can realize sequencing by performing multiple cycles of reactions through one-color (1-channel), two-color (2-channel) or four-color (4-channel) SBS, for example, determining the nucleotide or base type at a position on a nucleic acid molecule under test by adding four nucleotides in sequence for four base extensions (1-channel). Specifically, for example, four cycles of reactions are performed using four nucleotides carrying the same fluorescent label, one nucleotide is added for one cycle of reaction and a signal is collected, four cycles of reactions are performed to obtain a polymerization signal of the four nucleotides and thereby the nucleotide at one position on the template is determined, and then the multiple cycles of sequencing are repeated to determine the nucleotide composition of the nucleic acid molecule/nucleic acid fragment; for another example, every two of four nucleotides carry the same fluorescent label, and two nucleotides carrying different fluorescent labels are added in each cycle of reaction for reaction and signal detection; for yet another example, four nucleotides carry four different fluorescent labels, respectively, and four nucleotides are added in each cycle of reaction for reaction and signal detection.

The sources, specific structures or compositions of partial reagents involved in the examples are as follows: 3×SSC buffer, prepared by diluting 20×SSC buffer (Sigma, #S6639-1 L) with Rnase-free water.

Dimethyl squarate:

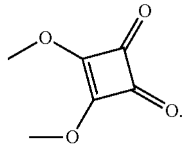

Polylysine (PLL):

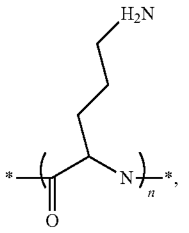

the degree of branching can be controlled between 0.35 and 0.45.

DBCO-PEG4-NHS:

D9:

(SEQ ID No. 1)

ttttttttttttccttgatacctgcgaccatccagttccactcagatgt gtataagagacag

P1:

(SEQ ID No. 2)

ttttttttttaatgatacggcgaccaccga

P2:

(SEQ ID No. 3)

ttttttttttcaagcagaagacggcatacga

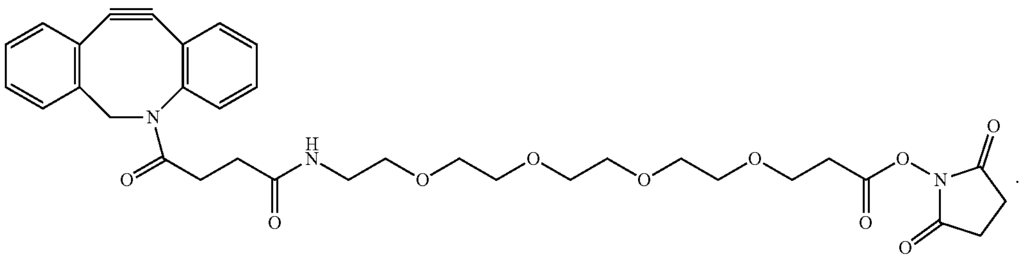 [SMILES: O=C(CCC(=O)N1Cc2ccccc2C#Cc2ccccc21)NCCOCCOCCOCCOCCC(=O)ON1C(=O)CCC1=O]

Chitosan:

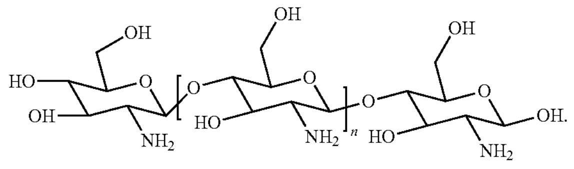

Diethyl squarate:

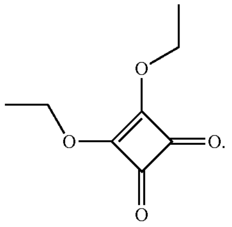

NHS-PEG4:

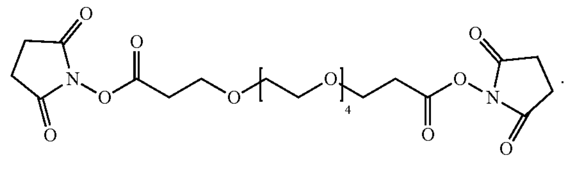

Example 10

This example describes the process and method for preparing a chip based on squaric acid and polylysine (PLL). The chip prepared by the method is used for single-molecule fluorescence sequencing after fluorescence density determination. The sequence of compound modification on the surface of the chip is as follows: coating aminosilane on a glass substrate through solution reaction, linking to a layer of squaric acid molecules through reaction with the amino group, linking to a layer of PLL through the squaric acid molecules, linking to NHS-DBCO through reaction with the amino group in the PLL, then blocking the amino groups that haven't participated in the reaction by using acetic anhydride, and finally linking to DNA molecules with azide functional groups through dibenzocyclooctyne (DBCO) functional groups. The prepared chip can be subjected to fluorescence density determination by using a GenoCare1600 single-molecule fluorescence sequencing platform, or can be used for nucleic acid sequencing on this platform.

The specific steps are as follows:

(1) Washing and activating the surface of glass (surface of substrate): the surface of glass (such as Schott D263M glass) was washed with ethanol and water alternately, and ultrasonic treatment was carried out simultaneously, where the ultrasonic treatment lasted for about 10 min, and the temperature of the ultrasonic bath was 37° C. After the completion of the washing, the surface of glass was activated with 0.5 M NaOH solution for 2 min to generate active hydroxyl groups on the surface of glass.

(2) Modifying with aminosilane: glacial acetic acid with a volume ratio of 0.1% was added into the water-ethanol mixed solution at a volume ratio of 1:20, and then (3-aminopropyl)triethoxysilane with a volume ratio of 2.5% was added to prepare an aminosilane modification solution. The activated glass sheet was immersed in the aminosilane modification solution and reacted at room temperature for 2 h. After the completion of the reaction, the glass sheet was washed with ethanol and water alternately and then dried in a vacuum oven at 110° C.

(3) Packaging the chip: reference could be made to disclosed content of, for example, WO2017205876A1, EP3590603A1 and the like for preparing chips having a chamber for holding liquid, a liquid inlet and a liquid outlet. For example, the glass sheet and a substrate layer etched with channels were bonded together to package a chip including a plurality of independent channels and having aminosilane modification on a specified surface. The channels were physically isolated and capable of independently holding solutions and controlling liquid feeding and liquid discharging as well as subsequent reactions. FIG. 1 is a schematic top view of a packaged chip having 16 channels. The channels had a length of 90 mm, a width of 1.8 mm and a height of 0.1 mm, and each channel was capable of independently controlling liquid feeding and liquid discharging as well as reactions. Depending on the requirements of detection throughput, the size and/or number of channels could be changed.

In the subsequent steps, various reaction reagents, washing reagents and the like could be introduced into the packaged channels by using liquid control equipment for further chemical modification/linking on a specified surface, which was beneficial for the batch preparation of chips and for obtaining a large number of chips with consistent surface property parameters.

(4) Modifying with squaric acid: 25 μL of 1 mM solution of dimethyl squarate in ethanol was introduced into each channel and reacted at room temperature for about 3 h. Then the channels were washed with ethanol. 200 μL of 0.1% aqueous PLL (with a molecular weight of 150-300 K) solution was added into 200 μL of ethanol, and the mixture was well mixed by vortexing and then introduced into channels at 25 μL per channel. The channel ports could be sealed (to prevent the solution from volatilizing), and then the chip was reacted in an oven at 37° C. for 3 h. After the completion of the reaction, 25 μL of 20 mM DBCO-PEG4-NHS solution prepared with 0.1 M $NaHCO_3$ (with a pH of about 8.3) buffer was introduced into each channel and reacted at room temperature for about 1 h. After the completion of the reaction, each channel could be washed with 1 mL of 3×SSC buffer. Then the acetic anhydride reaction solution (for example, by adding 1.75 μL of DIPEA (N,N-diisopropylethylamine) and 1 μL of acetic anhydride to 497.25 μL of formamide) was prepared. After being mixed well by vortexing, the reaction solution was immediately introduced into the channels at 25 μL per channel and reacted at room temperature for 15 min. After the completion of the reaction, each channel was washed with 1 mL of 3×SSC buffer.

(5) Linking a probe: a 5 nM $N_3$-D9 solution (the solvent was 3×SSC buffer, $N_3$ was linked/modifying azide at 5' end of D9, and D9 was the probe sequence (SEQ ID No. 1)) was introduced into the channels at 25 μL per channel, and the chip was reacted in an oven at 37° C. for about 16 h. After the completion of the reaction, each channel was washed once or multiple times with 1 mL of buffer containing 150 mM HEPES (4-hydroxyethylpiperazine ethanesulfonic acid) and 150 mM NaCl, and then optionally washed once or multiple times with 1 mL of 3×SSC buffer.

(6) Detecting amount/density of probe: a 2 nM D9'-Cy3 solution (the solvent was 3×SSC buffer, and D9' was reverse complementary sequence of D9) was introduced into the chip channels at 25 μL per channel, and the chip was placed in an oven at 40° C. for hybridization reaction for about 30 min. After the completion of the reaction, each channel was washed with 1 mL of 3×SSC buffer. The probe density on the surface of the chip prepared in this example was detected using the GenoCare1600 single-molecule fluorescence platform.

Figure 2:
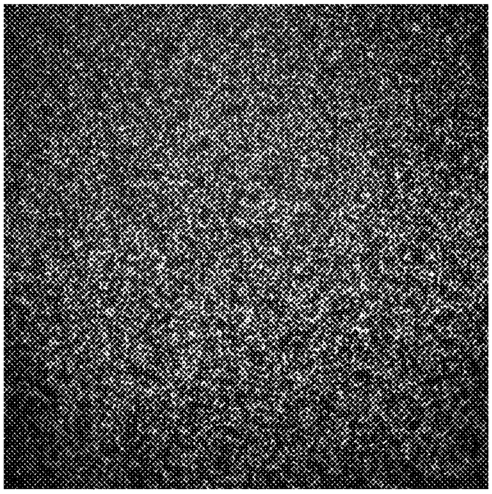
FIG. 2 is an image of a certain field of view on the surface of a chip according to an embodiment of the present application.

Specifically, the Cy3 fluorescence on the D9'-Cy3 chain was detected, and the average number of fluorescent dots (bright dots) in the photographed fields of view was used to evaluate the probe density on the surface of the chip. The number of fluorescent dots in each photographed field of view (FOV) with an area of 110×110 μm was counted in this example. The number of fluorescent dots in 100 fields of view in the middle area of each chip channel was obtained by photographing, and the number of fluorescent dots of an FOV was about 32,000-38,000 after averaging. As shown in FIG. 2, the average value of 16 channels is about 35,500.

The probe density on the surface of the chip prepared by the method can meet the requirements of a GenoCare1600 single-molecule sequencing platform.

Example 20

This example describes the process and method for preparing a chip based on squaric acid and polylysine (PLL). The chip prepared by the method is used for nucleic acid amplification on the surface of the chip and/or second-generation sequencing. The nucleic acid on the surface of the chip can be subjected to fluorescence intensity determination using a fluorescence microscope, or can be subjected to sequencing on a second-generation sequencing platform (such as the Illumina NextSeq 500 sequencing platform).

The specific steps are as follows:

(1) A chip with PLL modification on a specified surface was prepared by the same steps as steps (1)-(4) in Example 10, and then the chip was left to stand at room temperature for half an hour. Then the 10 μM $N_3$—P1 solution and the 10 μM $N_3$—P2 solution (the solvent was 3×SSC buffer, $N_3$ was linked/modifying azide functional group at 5' end of P1, and P1 (SEQ ID No. 2) and P2 (SEQ ID No. 3) were probe sequences) were mixed at a volume ratio of 1:1, and then the mixture was introduced into chip channels at 25 μL per channel. The liquid inlets and the liquid outlets of the channels were sealed, and the chip was reacted in an oven at 37° C. for about 16 h. After the completion of the reaction, each channel was washed with 1 mL of buffer containing 150 mM HEPES and 150 mM NaCl. Subsequently, 25 μL of 3 μM P1'-Cy3 solution (the solvent was 3×SSC buffer, and P1' was the reverse complementary sequence of P1) and 25 μL of P2'-Cy3 solution (P2' was the reverse complementary sequence of P2) were introduced into channel 1 and channel 2, respectively, and the chip was placed in an oven at 40° C. for hybridization reaction for about 30 min. After the completion of the reaction, the chip was naturally cooled to room temperature, and then each channel was washed with 1 mL of 3×SSC buffer. The liquid inlets and the liquid outlets of the chip were sealed for storage or for the use and detection in next step.

Figure 3:
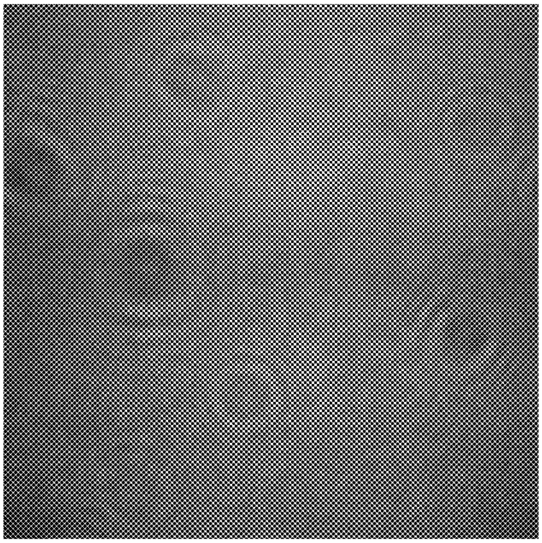
FIG. 3 is an image of a certain field of view on the surface of a chip according to an embodiment of the present application.

(2) The probe density on the surface of the chip prepared in this example was detected using the Illumina NextSeq 500 sequencing platform. Specifically, the Cy3 fluorescence on the P1'-Cy3 chain or the P2'-Cy3 chain was detected, and the overall average fluorescence brightness in the photographed fields of view was used to evaluate the probe density on the surface of the chip. The average fluorescence brightness in each photographed field of view (FOV) with an area of 110×110 μm was counted in this example. For channel 1, namely the channel for P1'-Cy3 hybridization, the average fluorescence brightness in an FOV was about 28,000 to 30,000. As shown in FIG. 3, the number of fluorescent dots in 100 fields of view in the middle area of each chip channel was obtained by photographing, and the average brightness of the whole channel was about 28,500 after averaging. For channel 2, namely the P2'-Cy3 hybridization channel, the average brightness measured was about 25,200. Therefore, under this measurement system, the fluorescence brightness corresponding to the average probe density of the whole channel (the sum of the average brightness values detected for P1'-Cy3 and P2'-Cy3) was 53,700.

(3) Removing hybrid chain with fluorescence: the hybridization chain with fluorescence was removed using formamide.

(4) Nucleic acid amplification and sequencing: the bridge PCR amplification was performed on the surface of the chip by taking a DNA library as a template to obtain an amplification cluster, which was labeled by using a hybridization chain with a fluorescent label and then subjected to detection on the Illumina NextSeq 500 sequencing platform.

Figure 4:
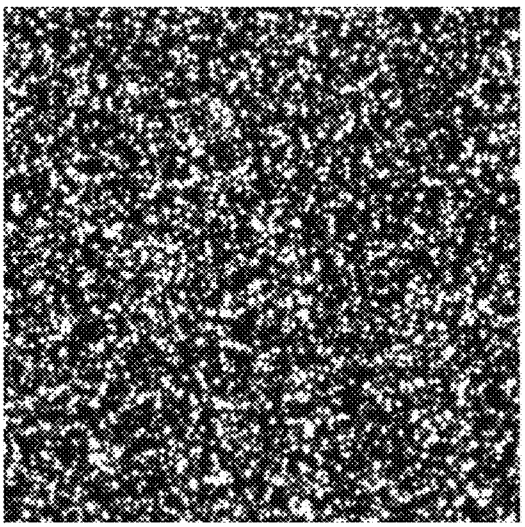
FIG. 4 is an image of a certain field of view on the surface of a chip according to an embodiment of the present application.

The detection results are shown in FIG. 4, and FIG. 4 shows the detection results of one of the channels obtained after being photographed. Then the amplification cluster could be subjected to sequencing on the IlluminaNextSeq 500 sequencing platform.

Example 30

This example describes the process and method for preparing a chip based on squaric acid and polylysine (PLL). The chip prepared by the method is used for isothermal amplification on the surface of the chip and/or second-generation sequencing.

The specific steps are as follows:

A chip was prepared by the same steps as steps (1)-(3) in Example 20, and then amplification was performed on the surface of the chip by taking a DNA library as a template and using reagents in the TwistAmp® Basic kit (TwistDx, Cambridge UK) to obtain an amplification cluster.

The operation steps are as follows: 29.5 μL buffer and nucleic acid-free water in the TwistAmp® Basic kit was added into 18 μL of DNA library that had become single-stranded by denaturation to allow the total volume to be about 50 μL, and the final concentration of the library was 10 μM. The mixture was shaken and centrifuged for a short time, and then 2.5 μL of magnesium acetate reagent was added. After being mixed well, the mixed reaction solution was introduced into the chip channels with a pipette. The chip was incubated at 37-42° C. for 15-30 min, and then each channel was washed with 1 mL of 3×SSC buffer. The amplification cluster obtained by amplification could be subjected to sequencing with the Illumina NextSeq 500 sequencing platform.

Example 40

This example describes the process and method for preparing a chip based on squaric acid and chitosan. The chip prepared by the method is used for single-molecule fluorescence sequencing, solid phase amplification on the surface of the chip and/or second-generation sequencing. The sequence of modification on the surface of the chip substrate (the chip substrate in this example is glass) is as follows: coating epoxy silane on the surface of the substrate through solution reaction, modifying the substrate with a layer of chitosan through the reaction of the epoxy groups and the amino groups in the chitosan, then linking to a layer of squaric acid molecules through the amino group reaction in the chitosan, then linking to DNA molecules with the $NH_2$ functional group by using the squaric acid molecules as the linking agent, and finally blocking the amino groups that haven't participated in the reaction with NHS-PEG4. The prepared chip can be subjected to fluorescence density determination using the Illumina NextSeq 500 fluorescence sequencing platform, namely determination of the density of nucleic acid molecules on the surface of the chip, then the nucleic acid amplification is performed by using template walking, and the obtained nucleic acid amplification cluster is used for subsequent sequencing.

The specific steps are as follows:

(1) Washing and activating the surface of glass (surface of substrate): the surface of glass (such as Schott D263M glass) was washed with ethanol and water alternately, and ultrasonic treatment was carried out simultaneously, where the ultrasonic treatment lasted for about 10 min, and the temperature of the ultrasonic bath was 37° C. After the completion of the washing, the surface of glass was activated with 0.5 M NaOH solution for 2 min to generate active hydroxyl groups on the surface of glass.

(2) Modifying with epoxy silane: the surface-activated glass sheet was immersed in a mixed aqueous solution of 3-glycidoxypropyl and hydroxypropyl trimethoxysilane (pH=5.5, at a volume ratio of 1:100) and reacted at room temperature for 8 h. After the completion of the reaction, the glass sheet was washed with ethanol and water alternately and then dried in a vacuum oven at 100° C.

(3) Packaging the chip: the surface was treated by a known packaging process to package the glass sheet and the substrate with the epoxy silane modification into a chip including a plurality of independent channels and having epoxy silane modification on a specified surface, and each channel in the chip was able to independently perform subsequent reaction. FIG. 1 is a schematic top view of a packaged chip having 16 channels. The channels had a length of 90 mm, a width of 1.8 mm and a height of 0.1 mm, and each channel was capable of independently controlling liquid feeding and liquid discharging as well as reactions. Depending on the requirements of detection throughput, the size and/or number of channels could be changed.

In the subsequent steps, various reaction reagents, washing reagents and the like could be introduced into the packaged channels by using liquid control equipment for further chemical modification/linking on a specified surface, which was beneficial for the automated preparation of chips, for obtaining a large number of chips with consistent surface property parameters, and for industrialization in chip preparation.

(4) Modifying with squaric acid: 25 μL of 0.1% chitosan (with a molecular weight of 160 K) solution prepared with 0.2 M carbonate buffer with a pH of 9.2 was introduced into each chip channel, and the channel ports were sealed (to prevent the solution from volatilizing). The chip was reacted in an oven at 37° C. for 16 h. After the completion of the reaction, each channel was washed with 1 mL of 3×SSC buffer. Then 25 μL of 1 mM solution of diethyl squarate in ethanol was introduced into each channel and reacted at room temperature for about 4 h. Then the channels were washed with ethanol.

(5) Linking a probe: 25 μL of 10 μM $NH_2$-A50 solution (prepared with 3×SSC and ethanol (at a volume ratio of 1:4) as the solvent) (in which $NH_2$ was the modifying/linked amino functional group at 5' end of A50, and A50 was a nucleic acid single strand formed by 50 adenine nucleotides) was introduced into each channel, and the chip was reacted in an oven at 37° C. for about 16 h. After the completion of the reaction, each channel was washed with ethanol and then washed with 1 mL of a buffer containing 150 mM HEPES and 150 mM NaCl. 25 μL of 20 mM NHS-PEG4 solution prepared with 0.1 M $NaHCO_3$ (with a pH of 8.3) buffer was introduced into each chip channel and reacted at room temperature for about 1 h to block the amino groups that hadn't participated in the reaction. After the completion of the reaction, each channel was washed with 1 mL of 3×SSC buffer.

(6) Detecting density of probe: a 3 μM T35-Cy3 solution (the solvent was 3×SSC buffer, Cy3 was the modifying Cy3 fluorophore at 3' end of T35, and T35 was a nucleic acid single strand formed by 35 thymine nucleotides) was introduced into channel 1 and channel 2 at 25 μL per channel, and the chip was placed in an oven at 40° C. for hybridization reaction for about 30 min. After the completion of the reaction, the chip was naturally cooled to room temperature, and then each channel was washed with 1 mL of 3×SSC buffer. The probe density on the surface of the chip prepared in this example was detected using the Illumina NextSeq 500 sequencing platform.

Figure 5:
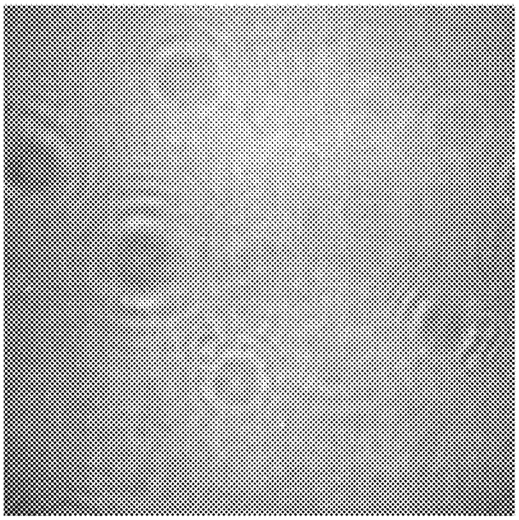
FIG. 5 is an image of a certain field of view on the surface of a chip according to an embodiment of the present application.

Specifically, the Cy3 fluorescence on the T35-Cy3 chain in the channel 1 and channel 2 was detected, and the average fluorescence brightness in the photographed fields of view was used to evaluate the immobilized density of the DNA chip. The average fluorescence brightness in each photographed field of view (FOV) with an area of 110×110 μm was counted in this example. By photographing 100 fields of view in the middle area of each of chip channel 1 and channel 2, it was obtained that the average fluorescence brightness in one FOV was 46,000-52,000. Values of all FOVs were averaged, and the average brightness of the channels was about 47,500, as shown in FIG. 5. Therefore, under this measurement system, the probe density of the whole channel corresponded to a fluorescence brightness of 47,500.

(7) Removing hybrid chain with fluorescence: the hybridization chain T35-Cy3 with fluorescence was removed using formamide.

Figure 6:
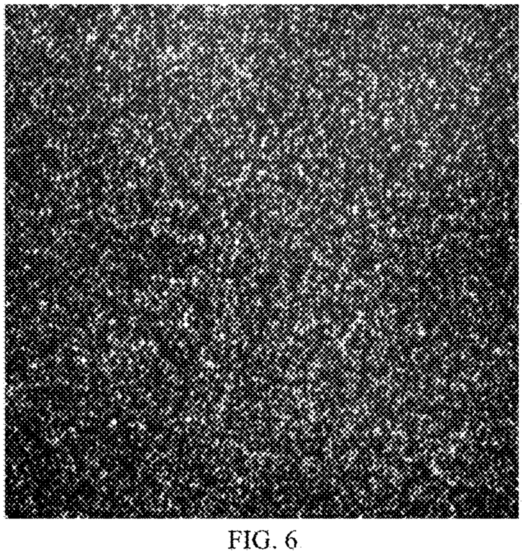
FIG. 6 is an image of a certain field of view on the surface of a chip according to an embodiment of the present application.

(8) Nucleic acid amplification and sequencing: the template walking solid phase amplification was performed on the surface of the chip by taking a DNA library as a template to obtain an amplification cluster, which was labeled by using a hybridization chain with a fluorescent label and then subjected to detection on the Illumina NextSeq 500 sequencing platform. The results are shown in FIG. 6. Then the amplification cluster could be subjected to sequencing on the Illumina NextSeq 500 sequencing platform.

Example 50

This example describes the process and method for preparing a chip based on squaric acid and amino substrate. The chip prepared by the method is used for single-molecule fluorescence sequencing. The sequence of compound modification on the surface of the chip is as follows: coating aminosilane on a glass substrate through solution reaction, linking to a layer of squaric acid molecules through reaction with the amino group, then linking to DNA molecules with $NH_2$ through the squaric acid molecules, and finally blocking the amino groups that possibly haven't participated in the reaction on the glass substrate by using NHS-PEG4. The prepared chip can be subjected to fluorescence density determination by using a GenoCare1600 single-molecule fluorescence sequencing platform, or can be used for sequencing on this platform.

The specific steps are as follows:

(1) Washing and activating the surface of glass (surface of substrate): the surface of glass (such as Schott D263M glass) was washed with ethanol and water alternately, and ultrasonic treatment was carried out simultaneously, where the ultrasonic treatment lasted for about 10 min, and the temperature of the ultrasonic bath was 37° C. After the completion of the washing, the surface of glass was activated with 0.5 M NaOH solution for 2 min to generate active hydroxyl groups on the surface of glass.

(2) Modifying with aminosilane: glacial acetic acid with a volume ratio of 0.1% was added into the water-ethanol mixed solution at a volume ratio of 1:20, and then (3-aminopropyl)triethoxysilane with a volume ratio of 2.5% was added to prepare an aminosilane modification solution. The activated glass sheet was immersed in the aminosilane modification solution and reacted at room temperature for 2 h. After the completion of the reaction, the glass sheet was washed with ethanol and water alternately and then dried in a vacuum oven at 110° C. for several hours.

(3) Packaging the chip: reference could be made to disclosed content of, for example, WO2017205876A1, EP3590603A1 and the like for preparing chips having a chamber for holding liquid, a liquid inlet and a liquid outlet. For example, a glass sheet having aminosilane modification on a specified surface was bonded to another substrate layer having channels etched on the surface thereof by using an adhesive substance such as glue to form a chip containing a plurality of channels. FIG. 1 is a top view of a packaged chip having 16 channels. The channels had a length of 90 mm, a width of 1.8 mm and a height of 0.1 mm, and each channel was capable of independently controlling liquid feeding and liquid discharging as well as reactions. Depending on the requirements of detection throughput, the size and/or number of channels could be changed.

In the subsequent steps, various reaction reagents, washing reagents and the like could be introduced into the packaged channels by using liquid control equipment for realizing chemical reactions on the surface of the chip.

(4) Modifying with squaric acid: 25 μL of 1 mM solution of dimethyl squarate in ethanol was introduced into each chip channel and reacted at room temperature for about 3 h.

Then the channels were washed 2-4 times with ethanol.

(5) Linking a probe: 25 μL of 10 nM $NH_2$-D9 solution (prepared with 3×SSC and ethanol (at a volume ratio of 1:4) as the solvent) (in which $NH_2$ was the modifying/linked amino functional group at 5' end of D9, and D9 was the probe sequence) was introduced into each chip channel, and the channel ports were sealed. The chip was reacted in an oven at 37° C. for about 16 h. After the completion of the reaction, each channel was washed with ethanol and then washed with 1 mL of a buffer containing 150 mM HEPES and 150 mM NaCl. 25 μL of 20 mM NHS-PEG4 solution prepared with 0.1 M $NaHCO_3$ (with a pH of 8.3) buffer was introduced into each chip channel and reacted at room temperature for about 1 h to block the amino groups that hadn't participated in the reaction before. After the completion of the reaction, each channel could be washed with 1 mL of 3×SSC buffer.

(6) Detecting density of probe: a 2 nM D9'-Cy3 solution (the solvent was 3×SSC buffer) was introduced into the chip channels at 25 μL per channel, and the chip was placed in an oven at 40° C. for hybridization reaction for about 30 min. After the completion of the reaction, each channel was washed with 1 mL of 3×SSC buffer. The probe density on the surface of the chip prepared in this example was detected using the GenoCare1600 single-molecule fluorescence platform. Specifically, the Cy3 fluorescence on the D9'-Cy3 chain was detected, and the number of fluorescent dots in the photographed fields of view was used to evaluate the immobilized density of the DNA chip. The number of fluorescent dots in each photographed field of view (FOV) with an area of 110×110 μm was counted in this example. 100 fields of view in the middle area of each chip channel were photographed, and the number of fluorescent dots of an FOV was about 39000 after averaging. The probe density on the surface of the chip prepared by the method can meet the requirements of a GenoCare1600 single-molecule sequencing platform.

Technical features in the above examples described above may be randomly combined. For simplicity of description, not all possible combinations of the technical features in the above examples are described. However, the combinations of the technical features are all to be considered as falling within the scope described in this specification provided that they do not conflict with each other.

The above examples illustrate several embodiments of the present application in detail, but they are not to be construed as a limit to the scope of the present application. It should be noted that various changes and modifications can be made by those of ordinary skill in the art without departing from the ideas of the present application, and these changes and modifications are all within the scope of the present application.

What is claimed is:

1. A chip, comprising:

a substrate having a surface grafted with an amino group, the amino group being a primary amino group or a secondary amino group; and a first compound grafted to the surface via the amino group, the first compound comprising the following structure:

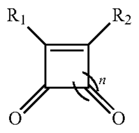

or

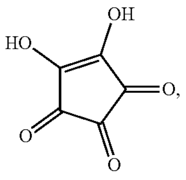

wherein $R_1$ and $R_2$ are each independently selected from —OH and C1-C5 alkoxy, and n is 1 or 2, a polymer linked to the first compound, wherein the polymer comprises a plurality of structural units, at least one of the structural units comprising an amino group; and a nucleic acid sequence linked to the polymer, the polymer and the nucleic acid sequence are linked via a linker group, wherein the linker group comprises a first terminus capable of bonding to the nucleic acid sequence and a second terminus capable of linking to the amino group of the polymer, the second terminus comprises at least one of —NHS, an epoxy group and

SEQUENCE LISTING

<160> NUMBER OF SEQ ID NOS: 3

<210> SEQ ID NO 1
<211> LENGTH: 61
<212> TYPE: DNA
<213> ORGANISM: Artificial Sequence
<220> FEATURE:
<223> OTHER INFORMATION: Sequence of adapter

<400> SEQUENCE: 1
tttttttttt tccttgatac ctgcgaccat ccagttccac tcagatgtgt ataagagaca 60
g 61

<210> SEQ ID NO 2
<211> LENGTH: 30
<212> TYPE: DNA
<213> ORGANISM: Artificial Sequence
<220> FEATURE:
<223> OTHER INFORMATION: Sequence of adapter

<400> SEQUENCE: 2
tttttttttt aatgatacgg cgaccaccga 30

<210> SEQ ID NO 3
<211> LENGTH: 31
<212> TYPE: DNA
<213> ORGANISM: Artificial Sequence
<220> FEATURE:
<223> OTHER INFORMATION: Sequence of adapter

<400> SEQUENCE: 3
tttttttttt caagcagaag acggcatacg a 31 an isocyanate group, and the nucleic acid sequence has a -DBCO or —$N_3$ modification, and the first terminus comprises -DBCO or —$N_3$.

2. The chip according to claim 1, wherein $R_1$ and $R_2$ are each independently selected from —OH, —$OCH_3$ and —$OCH_2CH_3$.

3. The chip according to claim 1, wherein the first compound comprises one of the following structures.

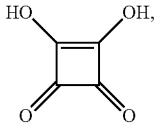

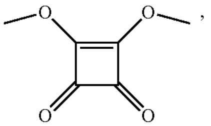

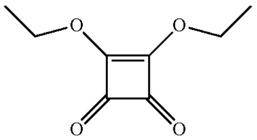

, and

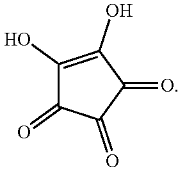

4. The chip according to claim 1, wherein the amino group is derived from at least one of aminosilane, polylysine, polyornithine, chitosan, polyamidoamine dendrimer, polyacrylamide and polyethyleneimine compounds.

5. The chip according to claim 4, wherein the amino group is derived from the aminosilane, optionally wherein the aminosilane is selected from at least one of (3-aminopropyl)triethoxysilane, 3-aminopropyl trimethoxysilane, 3-aminopropyl methyldiethoxysilane, and aminoethylaminopropyl triethoxysilane.

6. The chip according to claim 1, wherein the substrate having the surface grafted with the amino group comprises silane linked to the surface and a polymer linked to the surface via the silane, wherein the silane is selected from at least one of epoxy silane, alkenylsilane and alkynylsilane, and the polymer comprises a plurality of structural units, at least one of the structural units comprising the amino group, optionally wherein the polymer is selected from at least one of polylysine, polyornithine, chitosan, polyamidoamine dendrimer, polyacrylamide, and polyethyleneimine compounds.

7. The chip according to claim 6, wherein the silane comprises:

(a) the epoxy silane selected from at least one of 3-glycidoxypropyltrimethoxysilane, 3-glycidoxypropyltriethoxysilane, 3-glycidoxypropylmethyldiethoxysilane, and 3-glycidoxypropylmethyldimethoxysilane;

(b) the alkenylsilane selected from at least one of vinyltrimethoxysilane, vinyltriethoxysilane, vinyltris(2-methoxyethoxy) silane, and vinyltriisopropoxysilane; or (c) the alkynylsilane selected from at least one of propynyloxytrimethoxysilane and 2-propynyl [3-(triethoxysilyl) propyl]carbamate.

8. The chip according to claim 1, wherein the polymer is selected from at least one of polylysine, polyornithine, chitosan, polyamidoamine dendrimer, polyacrylamide and polyethyleneimine compounds.

9. A method for preparing a chip, comprising:

obtaining a substrate having a surface grafted with an amino group, the amino group being a primary amino group or a secondary amino group;

linking a first compound to the surface via the amino group, the first compound comprising the following structure:

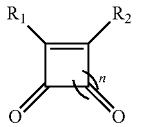

or

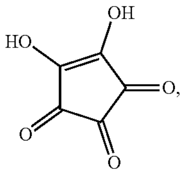

wherein $R_1$ and $R_2$ are each independently selected from —OH and C1-C5 alkoxy, and n is 1 or 2;

optionally wherein $R_1$ and $R_2$ are each independently selected from —OH, —$OCH_3$ and —$OCH_2CH_3$;

linking a polymer to the first compound, wherein the polymer comprises a plurality of structural units, at least one of the structural units comprising an amino group; and linking a nucleic acid sequence to the polymer via a linker group, wherein the linker group comprises a first terminus capable of linking to the nucleic acid sequence and a second terminus, preferably the second terminus comprises at least one of an —NHS group, an epoxy group and an isocyanate group, preferably the nucleic acid sequence has a -DBCO or —$N_3$ modification, and the first terminus comprises -DBCO or —$N_3$.

10. The method according to claim 9, wherein a reaction is performed at room temperature for 3-5 h to allow the amino group to be linked to the first compound.

11. The method according to claim 9, wherein the amino group is derived from an aminosilane, optionally wherein a reaction is performed at room temperature for 1-8 h to allow the aminosilane to be linked to the surface, in order to obtain the substrate with the surface grafting amino group;

optionally wherein the aminosilane is selected from at least one of (3-aminopropyl)triethoxysilane, 3-aminopropyl trimethoxysilane, 3-aminopropyl methyldiethoxysilane and aminoethylaminopropyl triethoxysilane.

12. The method according to claim 9, wherein the substrate having the surface grafted with the amino group comprises silane linked to the surface and a polymer linked to the surface via the silane, wherein the silane is selected from at least one of epoxy silane, alkenylsilane and alkynylsilane, and the polymer comprises a plurality of structural units, at least one of the structural units comprising the amino group;

(a) wherein a reaction is performed at 30-65° C. for 1-48 h to allow the polymer to be linked to the silane; optionally (b) wherein a reaction is performed at room temperature for 1-8 h to allow the silane to be linked to the surface.

13. The method according to claim 12, wherein the silane comprises:

(a) the epoxy silane selected from at least one of 3-glycidoxypropyltrimethoxysilane, 3-glycidoxypropyltriethoxysilane, 3-glycidoxypropylmethyldiethoxysilane and 3-glycidoxypropylmethyldimethoxysilane;

(b) the alkenylsilane selected from at least one of vinyltrimethoxysilane, vinyltriethoxysilane, vinyltris(2-methoxyethoxy) silane, and vinyltriisopropoxysilane; or (c) the alkynylsilane selected from at least one of propynyloxytrimethoxysilane and 2-propynyl [3-(triethoxysilyl) propyl]carbamate.

14. The method according to claim 9, wherein a reaction is performed at 30-80° C. for 1-48 h to allow the nucleic acid sequence to be linked to the first compound, optionally the method further comprising:

treating the surface with a blocking reagent selected from at least one of NHS-PEG4, NHS-PEG4-NHS, NHS-PEG-N3 and acetic anhydride.

15. The method according to claim 9, further comprising:

treating the surface with a blocking reagent selected from at least one of NHS-PEG4, NHS-PEG4-NHS, NHS-PEG-N3 and acetic anhydride.

16. The method according to claim 15, (a) wherein a reaction is performed at 30-65° C. for 1-48 h to allow the first terminus of the linker group to be linked to the nucleic acid sequence;

(b) wherein a reaction is performed at room temperature for 0.5-5 h to allow the second terminus of the linker group to be linked to the amino group of the polymer;

(c) wherein the polymer is selected from at least one of polylysine, polyornithine, chitosan, polyamidoamine dendrimer, polyacrylamide and polyethyleneimine compounds, wherein a reaction is performed at 30-40° C. for 1-5 h to allow the polymer to be linked to the first compound; or any combination of (a), (b), and (c).

17. A method for detecting nucleic acid, comprising a step of contacting the chip of claim 1 and detecting the nucleic acid.

18. The method according to claim 17, comprising sequencing the nucleic acid.

19. The method according to claim 9, wherein the first compound is selected from one of the following compounds:

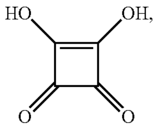,
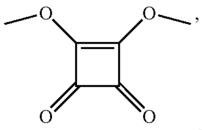,
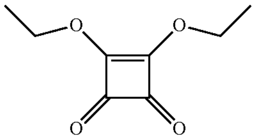
and
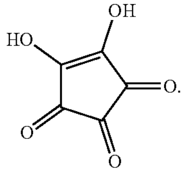.

* * * * *